United States Patent
Mohs et al.

(10) Patent No.: US 10,272,088 B2
(45) Date of Patent: Apr. 30, 2019

(54) FAS INHIBITORS AND METHODS ASSOCIATED THEREWITH

(71) Applicant: Wake Forest University Health Sciences, Winston-Salem, NC (US)

(72) Inventors: Aaron M. Mohs, Omaha, NE (US); Steve J. Kridel, Clemmons, NC (US); Tanner K. Hill, Omaha, NE (US)

(73) Assignee: Wake Forest University Health Sciences, Winston-salem, NC (US)

( * ) Notice: Subject to any disclaimer, the term of this patent is extended or adjusted under 35 U.S.C. 154(b) by 0 days.

(21) Appl. No.: 15/328,797

(22) PCT Filed: Jul. 25, 2015

(86) PCT No.: PCT/US2015/042141
§ 371 (c)(1),
(2) Date: Jan. 24, 2017

(87) PCT Pub. No.: WO2016/076924
PCT Pub. Date: May 19, 2016

(65) Prior Publication Data
US 2017/0360789 A1    Dec. 21, 2017

Related U.S. Application Data

(60) Provisional application No. 62/028,968, filed on Jul. 25, 2014.

(51) Int. Cl.
| | |
|---|---|
| *A61K 31/519* | (2006.01) |
| *A61K 31/085* | (2006.01) |
| *A61K 31/336* | (2006.01) |
| *A61K 31/341* | (2006.01) |
| *A61K 31/352* | (2006.01) |
| *A61K 31/365* | (2006.01) |
| *A61K 31/4965* | (2006.01) |
| *A61K 45/06* | (2006.01) |
| *A61K 9/51* | (2006.01) |
| *A61K 47/61* | (2017.01) |
| *A61K 47/69* | (2017.01) |
| *A61K 31/353* | (2006.01) |
| *A61K 31/366* | (2006.01) |

(52) U.S. Cl.
CPC .......... *A61K 31/519* (2013.01); *A61K 9/5146* (2013.01); *A61K 31/085* (2013.01); *A61K 31/336* (2013.01); *A61K 31/341* (2013.01); *A61K 31/352* (2013.01); *A61K 31/353* (2013.01); *A61K 31/365* (2013.01); *A61K 31/366* (2013.01); *A61K 31/4965* (2013.01); *A61K 45/06* (2013.01); *A61K 47/61* (2017.08); *A61K 47/6939* (2017.08)

(58) Field of Classification Search
CPC ................ A61K 31/519; A61K 31/341; A61K 47/6939; A61K 31/366
See application file for complete search history.

(56) References Cited

PUBLICATIONS

Choi, K. Y, et al.; title: Smart Nanocarrier Based on PEGylated Hyaluronic Acid for Cancer Therapy, ACS Nano 2011, 5, (11), 8591-8599. (Year: 2011).*
Authors: J. A. Menendez, et al.; title: Antitumoral actions of the anti-obesity drug orlistat (Xenical™) in breast cancer cells: oncogene; Annals of Oncology, vol. 16, Issue 8, pp. 1253-1267, Published: May 3, 2005. (Year: 2005).*
Authors: Hwankyu Lee, et al.; title: Molecular Dynamics Studies of Polyethylene Oxide and Polyethylene Glycol: Hydrodynamic Radius and Shape Anisotropy; Biophys J. Aug. 15, 2008; 95(4); pp. 1590-1599; Published online May 2, 2008. (Year: 2008).*
Authors: Eliska Vaculikova, et al.; tile: Primary investigation of the Preparation of Nanoparticles by Precipitation; Molecules 2012, 17, 11067-11078; published Sep. 13, 2012. (Year: 2012).*
Finelli et al.; Title: A new viscosupplement based on partially hydrophobic hyaluronic acid: a comparative study; Biorheology; vol. 48 , No. 5, pp. 263-275, published 2011. (Year: 2011).*

* cited by examiner

*Primary Examiner* — Yanzhi Zhang
(74) *Attorney, Agent, or Firm* — Fox Rothschild LLP

(57) ABSTRACT

The present invention relates to compounds, compositions and methods comprising nanoparticles (NP) that are based on hyaluronic acid (HLA) that have been modified with hydrophobic moieties that can entrap FASN inhibitor compounds. In one embodiment, the FASN inhibitor compounds include Orlistat. In one embodiment, the hydrophobic moieties comprise 5-βCA, Pba, or ODA, or combinations thereof. In a variation, the present invention relates to a composition comprising NPs based upon HLA, Orlistat, one or more of the hydrophobic moieties comprising 5-βCA, Pba, or ODA, and one or more of members selected from the group consisting of PEG and a dilute solution containing SDS.

22 Claims, 7 Drawing Sheets

FAS INHIBITORS AND METHODS ASSOCIATED THEREWITH

The present invention claims priority under 35 USC 371 to PCT application No. PCT/US15/42141 filed Jul. 24, 2015 and under 119(e) to U.S. Provisional Application No. 62/028,968, filed Jul. 25, 2014, the entire contents of both of which are incorporated by reference in their entireties.

FIELD OF THE INVENTION

The present invention relates to compounds, compositions and methods related to new cancer treatment. In an embodiment, the present invention relates to the development and use of newly developed nanoparticles and/or compositions for treatment of cancer.

BACKGROUND OF THE INVENTION

Fatty acid synthase (FASN) is a 250-270 kDa enzyme that uses endogenous carbon sources, e.g. acetyl-CoA and Malonyl-CoA for the production of fatty acids (FAs), primarily palmitate. FASN has six independent catalytic domains, providing fertile opportunity for drug development. In benign cells and tissues, dietary lipids are predominantly utilized for the production of new lipids and FASN has a minor role in the production of FAs. Increased de novo synthesis of fatty acids is characteristic of tumorigenesis and is closely related to the glycolytic pathway. Tumor cells shift from oxidative to glycolytic metabolism, which feeds excess pyruvate to drive de novo FA synthetic pathway to fulfill the increased lipid requirements for aberrant cellular proliferation. As a consequence, FASN has increased expression and activity in tumor cells that correlates with advanced tumor stage and grade, poor patient prognosis, and disease-free survival.

A number of FASN inhibitors have been developed with a wide array of chemical structures, including compounds with long aliphatic groups, curcuminoids, and polyphenolic compounds. However, these compounds are either in early stages of preclinical development or are limited by severe side-effects.

Alternatively, it was discovered that Orlistat is a particularly effective FASN inhibitor. Orlistat (FIG. 2B) is a lipstatin analog, acts as a lipase inhibitor, and is FDA-approved as a weight loss aid to block the absorption of dietary fat. Crystallographic studies have shown that Orlistat inhibits FASN by directly interacting with the thioesterase domain. The major challenge in the further development of Orlistat as a highly promising chemotherapeutic agent is its high hydrophobicity and poor bioavailability. This results in the need to use extremely large doses to generate a tumor response in mice, which could incur undesirable side effects.

Nanometer-sized particles, approximately 10-100 nm, have functional and structural properties that are not available from either small molecules or from bulk materials. For example, nanoparticles (NP) have a large surface area to volume ratio, which allows the conjugation of tumor-specific targeting ligands (e.g. small molecules, peptides, or antibodies), therapeutics, or diagnostic agents. One recent advancement has been the development of biodegradable NPs with increased therapeutic loading capacity for drug delivery. Thus, development of biocompatible NPs for targeted therapy is an area of considerable interest. While several types of NPs, such as quantum dots, gold, or iron oxide, result in a wealth of properties that can be precisely tuned, these NPs can remain in the body for prolonged times and thus, most of the work related to metallic nanoparticles is still in preclinical development. Consequently, the majority of NPs in clinical trials are based on polymers of liposomes.

As of 2012, six NP drug formulations for cancer therapy are FDA-approved and used in clinics, while more than a dozen more are in clinical use for other diseases and conditions. Due to their mesoscopic size, NPs are preferentially accumulated in tumor stroma due to increased vascular permeability and poor lymphatic drainage out of tumors, which is commonly referred to as the enhanced permeability and retention (EPR) effect. Tumor accumulation can further be increased by conjugation of tumor-specific targeting ligands that can improve intracellular accumulation, drug efficacy, and reduce off-target toxicity. Example targeted, macromolecular FDA-approved therapies, include imatinib for chronic myeloid leukemia and trastuzumab for human epidermal growth factor-2 (HER-2) positive breast cancer.

It is believed that FASN inhibitors could provide an effective means of chemotherapy by stopping production of FAs needed for new cells.

Hyaluronic acid is a ligand for the transmembrane receptor, CD44. Native CD44 along with its various isoforms e.g. CD44v6, can be found to various degrees on benign and malignant cells. CD44 has been shown to be a common marker for tumor progenitor cells as well as cells of colon, head and neck, hepatocellular, non-small cell lung, prostate and breast cancer. HLA is readily catabolized by hyaluronidases (HYAL), primarily HYAL-1 and HYAL-2. Both CD44 and HYAL are upregulated in malignant tissue and HYAL associated with malignant tumors is several times more active, especially in prostate tumors. Thus, HLA renders a NP targeted to CD44 and biodegradable in the tumor microenvironment.

HLA has been conjugated to various hydrophobic ligands such as ceramide, bile acids, or poly [lactide-(co-glycolic acid)] to drive self-assembly into nanoparticles for targeted delivery of chemotherapeutic drugs, such as paclitaxel and doxorubicin. It has been revealed that diminished uptake of HLA-butyric acid-fluorescein conjugates occur when CD44+ MCF-7 cells were pretreated with anti-CD44 MAbJ173 antibody.

Recently, Amiji and colleagues developed a library of HLA (20 kDa) NPs modified with various hydrophobic ligands and cationic moieties for siRNA delivery to lung, breast, liver, and melanoma tumor models. Interestingly, HLA conjugates showed that gene silencing activity in vitro and in vive was linear with CD44 expression.

BRIEF SUMMARY OF THE INVENTION

In one embodiment, the present invention relates to NPs that are based on hyaluronic acid (HLA) that are highly promising for delivery of chemotherapeutic compounds. HLA is a non-sulfated glycosaminoglycan (GAG) comprising disaccharide repeat units of alternating (1-3)-β linked N-acetyl-D-glucosamine and (1-4)-β linked D-glucuronic acid (FIG. 2A). HLA is present in the extracellular matrix at very high concentration (2.5 g/l) and plays an important role in cell proliferation, differentiation and tissue repair, and is present in synovial fluid, umbilical cord, and vitreous humor of the eye. Due to its biocompatibility, HLA is found clinically in many treatments, including, ophthalmology, orthopedic surgery, rheumatology, otolaryngology, dermatology, and plastic surgery as well as dressings for wound healing.

In an embodiment, the present invention relates to the development and optimization, in vivo, of a newly designed nanoparticle-based drug delivery system that increases the solubility, stability, and efficacy of Orlistat.

In an embodiment, the present invention relates to using NPs that are based on hyaluronic acid to deliver anti-cancer drugs or chemotherapeutic agents to cancer cells. In addition to its widespread clinical use, HLA has two additional compelling properties as a carrier for chemotherapeutic agents. First, HLA is a ligand for the transmembrane receptor, CD44. Native CD44 along with its various isoforms e.g. CD44v6, can be found to various degrees on benign and malignant cells. CD44 has been shown to be a common marker for tumor progenitor cells as well as cells of colon, head and neck, hepatocellular, non-small cell lung, prostate and breast cancer. Second, HLA is readily catabolized by hyaluronidases (HYAL), primarily HYAL-1 and HYAL-2. Both CD44 and HYAL are upregulated in malignant tissue and HYAL associated with malignant tumors is several times more active, especially in prostate tumors. Thus, HLA renders a NP targeted to CD44 and biodegradable in the tumor microenvironment.

Thus, in an embodiment, the present invention relates to an exciting new class of chemotherapeutic FASN inhibitors. In general, in one variation, the compounds, compositions and/or methods relate to improvements on these inhibitors which are known to be very hydrophobic with poor tumor distribution and bioavailability. Thus, in one embodiment, the present invention relates to innovative aspects that would advance the translation of FASN inhibitors.

Orlistat is already FDA-approved for another use, and its ability to inhibit FASN was first demonstrated by the present inventors. Thus, in one embodiment, the present invention relates to changing the formulation of Orlistat for improved tumor delivery, which will likely have a dramatic advantage compared to the translational development of a new class of FASN inhibitors. In a variation, the present invention relates to encapsulation of various drugs including Orlistat into a precisely engineered NP. Based on data presented in the present application, the inventors believe that this will increase the solubility and stability of Orlistat, which could dramatically increase its in vivo efficacy and minimize side effects. The use of hydrophobically modified HLA introduces molecular targeting to CD44 and precise degradation due to HYAL, which the inventors believe will result in controlled orlistat delivery. In a further embodiment, the present invention relates to NP entrapment of FASN inhibitors and the development of new NPs, which could benefit the delivery of a number of hydrophobic compounds, including the experimental FASN inhibitors mentioned above.

DETAILED DESCRIPTION OF THE INVENTION

Figure 1:
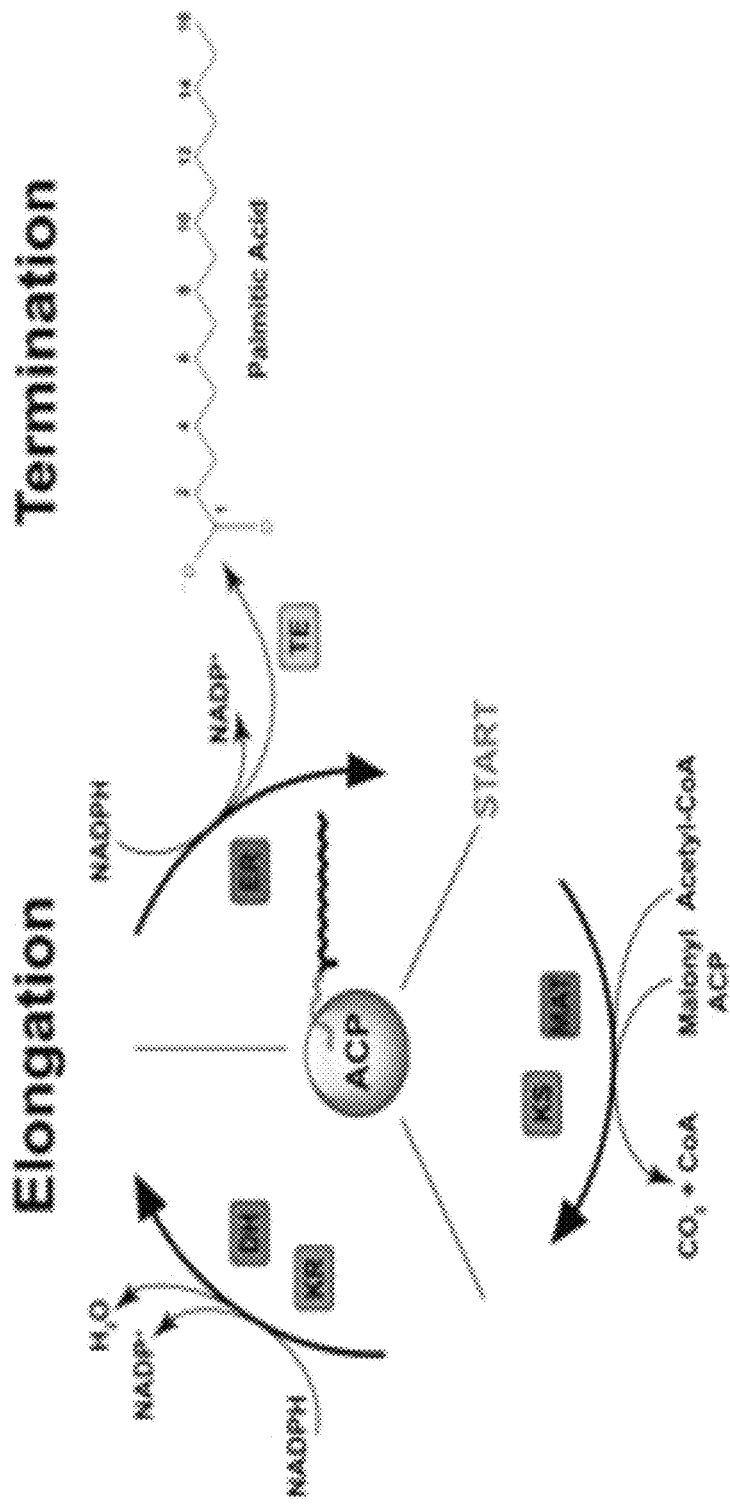
FIG. 1 shows the reaction pathway of fatty acid synthase (FASN).

In one embodiment, the present invention relates to nanoparticles (NP) that are based on hyaluronic acid (HLA) that have been modified with hydrophobic moieties that can entrap other compounds such as the FASN inhibitor, Orlistat, herein referred to as "Nano-Orl". In an embodiment, the present invention presents data that shows that such NPs have been designed, characterized, and evaluated as promising through a series of in vitro assays. In a variation, the present invention relates to not only the modified nanoparticles, but also compositions and methods using these NPs.

Furthermore, in an embodiment, using a model near infrared fluorophore, indocyanine green (ICG), the inventors have demonstrated that these nanoparticles can be targeted to CD44 positive tumor cells and have preferential distribution to tumors in vivo. In one embodiment, Nano-Orl has been evaluated in human tumor xenograft models and further optimized so as to have an ideal controlled release of Orlistat from Nano-Orl. These data are presented below that support the overall approach.

Synthesis of Nano-Orl Based on Hydrophobic Modification of HLA.

HLA-based NPs were synthesized by first conjugating a hydrophobic ligand, either 5-β-cholanamide (5-βCA), 4-(pyrene-1-yl)butanamide (PBA), or octadecylamine (ODA), to HLA via N-hyrdoxysuccinimide (NHS) and N-(3-dimethylaminopropyl)-N'-ethylcobodiimide hydrochloride (EDC). FIG. 2A shows the chemical structures of these NP components. 5-βCA and PBA were first synthesized from their acid precursors based on a method described in the literature (see Jin Y-J, 2012). Several conjugation ratios, as determined by $^1$H-NMR, of PBA and 5-βCA on to HLA were synthesized, including 6 and 10 weight %, while ODA was 2.5 weight %. Next amphiphilic-HLA was dissolved in an EtOH/H$_2$O mixed solvent and Orlistat, dissolved in EtOH, was added to the solution. The mixture was dialyzed against 18.2 MΩ water to drive self-assembly and entrapment of Orlistat in the hydrophobic core, which is shown schematically in FIG. 2B. The resulting nanoparticles, Nano-Orl, were 150-300 nm in hydrodynamic diameter (HD) as determined by dynamic light scattering and depended on the hydrophobic ligand. An example of the HD distribution is given in FIG. 2C, where PBA is the hydrophobic ligand (HD=197±4 nm), whereas nanoparticles with ODA as the hydrophobic ligand approached 300 nm HD.

After Nano-Orl was synthesized and characterized, it was subjected to in vitro cytotoxicity assays to confirm that it was as efficacious as free Orlistat. Cytotoxicity was assessed by first incubating PC3 prostate, RKO colorectal, and MDA-MB-231 breast cancer cells in a 96 well plate (2000 cells/well) with Nano-Orl (PBA hydrophobic ligand), Orlistat, or media controls. Media alone or containing experimental or control agents was refreshed after 24 h and allowed to incubate for 24 additional hours. Cytotoxicity was then evaluated using the WST-8 assay (Dojindo, Rockville, Md.). Nano-Orl was dosed equivalent to 25 m Orlistat. FIG. 3A. shows that Nano-Orl resulted in 10-40% viability relative to the NP vehicle media control, which was consistent with free Orlistat; (HLA-PBA with no Orlistat has no cytotoxicity). Furthermore, using methods published by Kridel (co-I) and colleagues, a $^{14}$C-acetate incorporation study was performed to determine if FASN inhibition contributed to the cytotoxicity to the same extent as free Orlistat. Nano-Orl did prevent $^{14}$C-acetate incorporations as shown in FIG. 3B, which is indicative of FASN inhibition.

Figure 4:
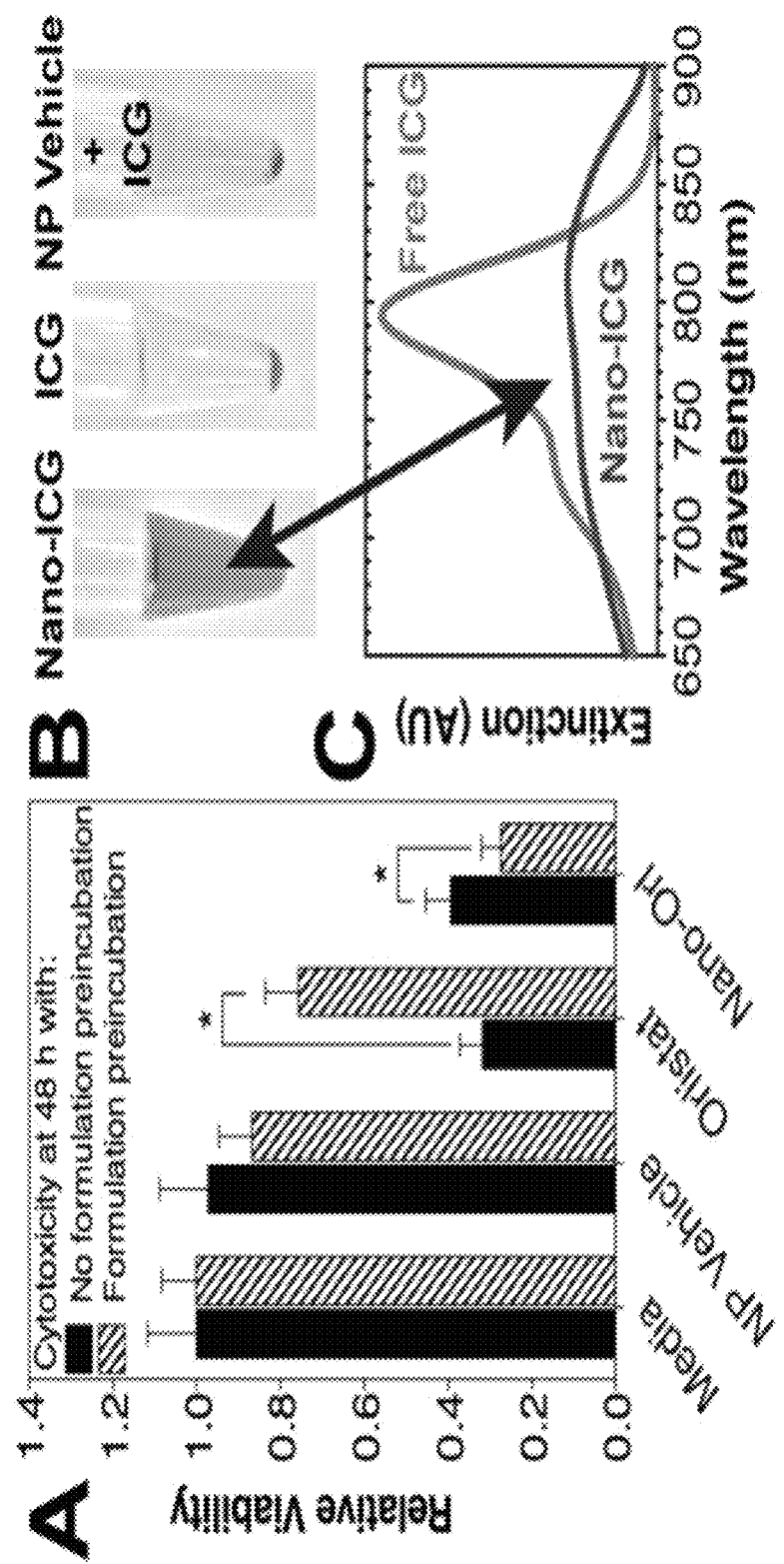
FIG. 4 shows Confirmation that Orlistat is entrapped in Nano-Orl. (A) Nano-Orl retains its cytotoxicity after pre-incubation prior to incubation with cells, whereas Orlistat is rendered ineffective. (B) ICG shows that amphiphilic molecules can be trapped in PBS. This is supported by extinction spectra showing close ICG packing (C). Free ICG and ICG physically mixed with HLA-based NPs immediately aggregate.

Since Nano-Orl and Orlistat had comparable in vitro toxicity, a subsequent study was performed to confirm that Orlistat was entrapped in NPs. Hydrolysis of the β-propriolactone ring affects binding to FASN. Orlistat in Nano-Orl should be protected from hydrolytic degradation because it is trapped in a hydrophobic pocket. Accordingly, studies were performed wherein both Orlistat and Nano-Orl were pro-incubated in PBS prior to incubating with cells. FIG. 4A shows that pro incubation of Orlistat dramatically reduces its efficacy, while the Nano-Orl molecule remains cytotoxic, suggesting that Orlistat is readily entrapped in the Nano-Orl. This is consistent with studies using the amphiphilic dye, indocyanine green (ICG), which more visibly makes this point. ICG is not soluble in PBS. FIG. 4B shows that ICG remains soluble in PBS when entrapped in a nanoparticle (entrapment is further supported in FIG. 4C, which shows a scattered extinction spectra indicative of close ICG packing). Free ICG or ICG mixed with NP rapidly aggregates in PBS and can be centrifuged out. FIG. 4 shows that Orlistat (and other hydrophobic compounds) can be entrapped in HLA-based NPs. Accordingly, in one aspect of the invention, the present invention relates to compositions comprising Orlistat and other hydrophobic compounds entrapped in HLA-based NPs.

Figure 5:
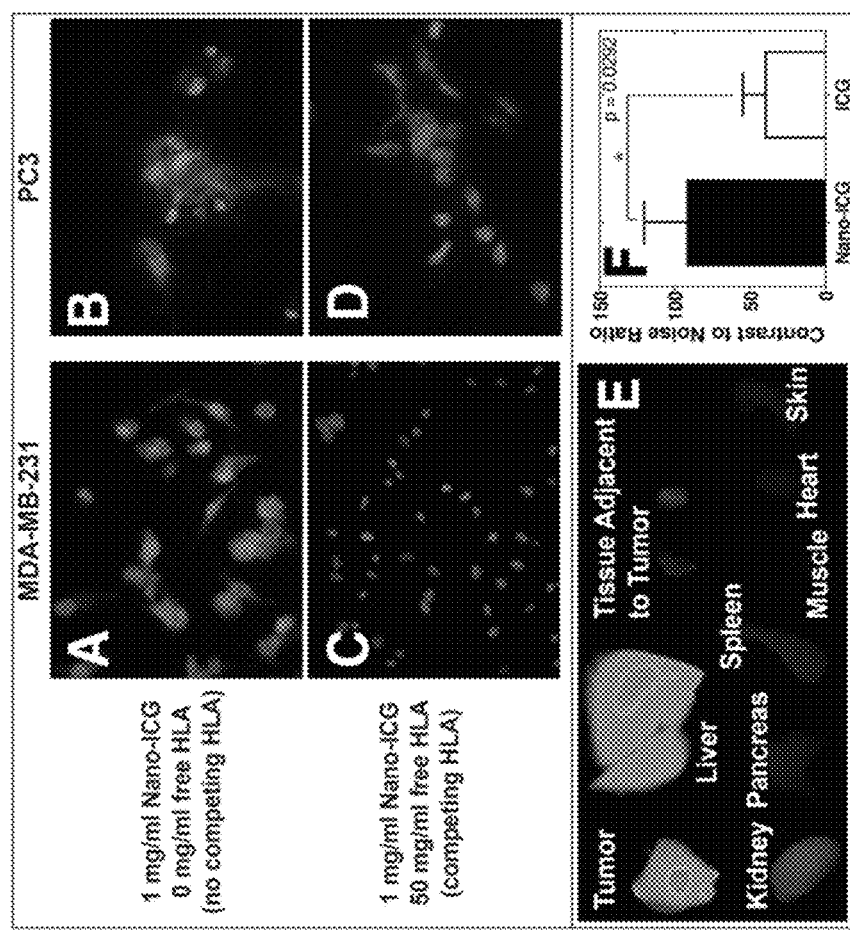
FIG. 5 shows MDA-MB-231 and PC3 cells (A,B) were incubated with Nano-ICG (a model for Nano-Orl), which is rapidly uptaken by these CD44 positive cells. Uptake is inhibited by competition for the CD44 receptor by HLA (C,D). Using an MDA-MB-231 tumor model, Nano-ICG has a preferentially distribution to tumors (E) and when compared to systemic injection of free ICG (F), Nano-ICG provides significantly stronger signal.

As described above, HLA is valuable as a central component of the NP delivery system because HLA is a primary ligand for CD44 and HLA can be degraded by hyaluronidases (HYAL); both CD44 and HYAL are overexpressed in many tumors. Thus, in one embodiment, the present invention relates to using the NP delivery system that comprises HLA. The results shown in FIG. 5 demonstrate the advantages of using HLA-based NPs. Using HLA-based NPs loaded with ICG as a model, CD44 positive (MDA-MB-231 breast and PC3 prostate) tumors rapidly uptake the dye-loaded NPs (FIG. 5A,B); the NIR fluorescence is pseudo-colored red.

Uptake, however, can be inhibited by incubating with an excess of competitive ligand, in this case free HLA (see FIGS. 5C and D; shown as a decrease in NIR signal). Moreover, the level of NIR fluorescence in cells was inversely proportional to the concentration of free HLA (results not shown). An in vivo experiment in mice bearing MDA-MB-231 tumor xenografts shows that Nano-ICG (PBA was hydrophobic ligand) preferentially accumulates in tumors (see FIG. 5E). Accumulation is also seen in the liver, the known clearance route of ICG. Comparing Nano-ICG to free ICG injection, Nano-ICG produces significantly higher tumor contrast (see FIG. 5F). The ability for HLA-based NPs to alter biodistribution is expected to be even more profound for Orlistat since it cannot be administered intravenously. These data provide proof of feasibility for encapsulating Orlistat in the Nano-Orl system.

In Vivo Efficacy of HLA-NP Entrapped Orlitat (Nano-Orl)

In one embodiment, Nano-Orl will be tested in a human prostate tumor xenograft. The data suggest that Orlistat entrapped in NPs will be as toxic as free Orlistat, but will have increased solubility and stability compared to Orlistat. Thus, in one aspect of the invention, the present invention relates to providing a composition for treating cancer with improved solubility relative to the presently available vehicles. In vivo studies regarding Nano-Orl will be performed to set a benchmark of its efficacy. The therapeutic efficacy will rationally guide synthetic modification to Nano-Orl. Thus, in one embodiment, the present invention relates to being able to increase and/or decrease solubilities of compounds in combination with NPs that will either increase or decrease the therapeutic efficacy. In a variation, the following experiments will be performed: (1) Develop a quantitative and reproducible method to quantitate Orlistat loading in NPs, (2) measure tumor inhibition/reduction due to Nano-Orl relative to Orlistat, while closely monitoring the overall health of the tested subjects (e.g., animals). In an embodiment, the present invention will allow the realization of detailed pharmacokinetic, biodistribution, and toxicity studies. In a variation, these detailed pharmacokinetic, biodistribution, and toxicity studies will provide for more efficacious treatment.

Establish Quantitative Method for Orlistat Loading into NPs

In an embodiment, Nano-Orl will undergo rigorous evaluation to identify a characterization method that reproducibly quantifies Orlistat loading. HLA that has been modified with PBA will be one Nano-Orl formulation that is evaluated. Orlistat loading will be quantified by using HPLC using a C18 column and an acetonitrile/water (950:50, v/v) mobile phase for initial conditions. To evaluate whether NP entrapment of Orlistat interferes with HPLC analysis, several solvent systems will be tested to completely solubilize both Orlistat and amphiphilic HLA. In one embodiment of the present invention, detection will be tested at 205 nm, which could have multiple interfering signals. Therefore, HPLC-MS will be used to first validate the solvent system for Orlistat isolation. Nano-Orl will undergo further evaluation to quantify HD by both DLS and by size exclusion chromatography (SEC).

Evaluate the Vivo Therapeutic Efficacy Nano-Orl Using Tumor Xenografts in Mice

Using mice bearing human prostate tumor xenografts, Nano-Orl will be evaluated as a drug delivery vehicle for Orlistat to inhibit tumor growth and eradicate the disease. PC3 cells will be used for these tumors because they have been extensively studied for response to Orlistat and other FAS inhibitors. PC3 cells ($5\text{-}10 \times 10^6$) will be injected into the flank of male nude mice aged 8-12 weeks and will be allowed to grow until they reach approximately 100-300 mm³. Tumors will then be treated with Orlistat, Nano-Orl, NP vehicle, formulation buffer and no treatment controls. Orlistat will be formulated with 33% ethanol and 66% PEG 400 and be administered IP with a dose of 240 mg/kg/day every day for 28 days; both the formulation and dose are consistent with the literature. Lead Nano-Orl (based upon in vitro studies that will be HLA modified with PBA) will be administered systemically via a tail vein. IP administration of NPs can result in the NP being entrapped in the lymphatics, which would further decrease bioavailability of Orlistat; thus, Nano-Orl will be administered intravenously. Because it is believed that systemic delivery of Nano-Orl will result in higher Orlistat biodistribution to the tumor, three doses of Nano-Orl, normalized to Orlistat; 240 mg/kg, 120 mg/kg, and 60 mg/kg, will be tested. Consistent with other NP chemotherapeutic formulations that have been used to treat tumor xenografts, Nano-Orl will be administered every 4 days for 28 days (7 IV administrations). The treatment efficacy will be determined by calculating tumor volume using the following the formula: $V = \pi/6 \times X \times Y^2$ wherein V is the volume and X is the depth of the tumor and Y is the other dimension(s) of the tumor (e.g., length and/or width). Mice will be monitored for weight loss, labored breathing, hunched posture, etc. to ensure that the studies meet vertebrate justification parameters (e.g., the ethical treatment of research animals).

Figure 2:
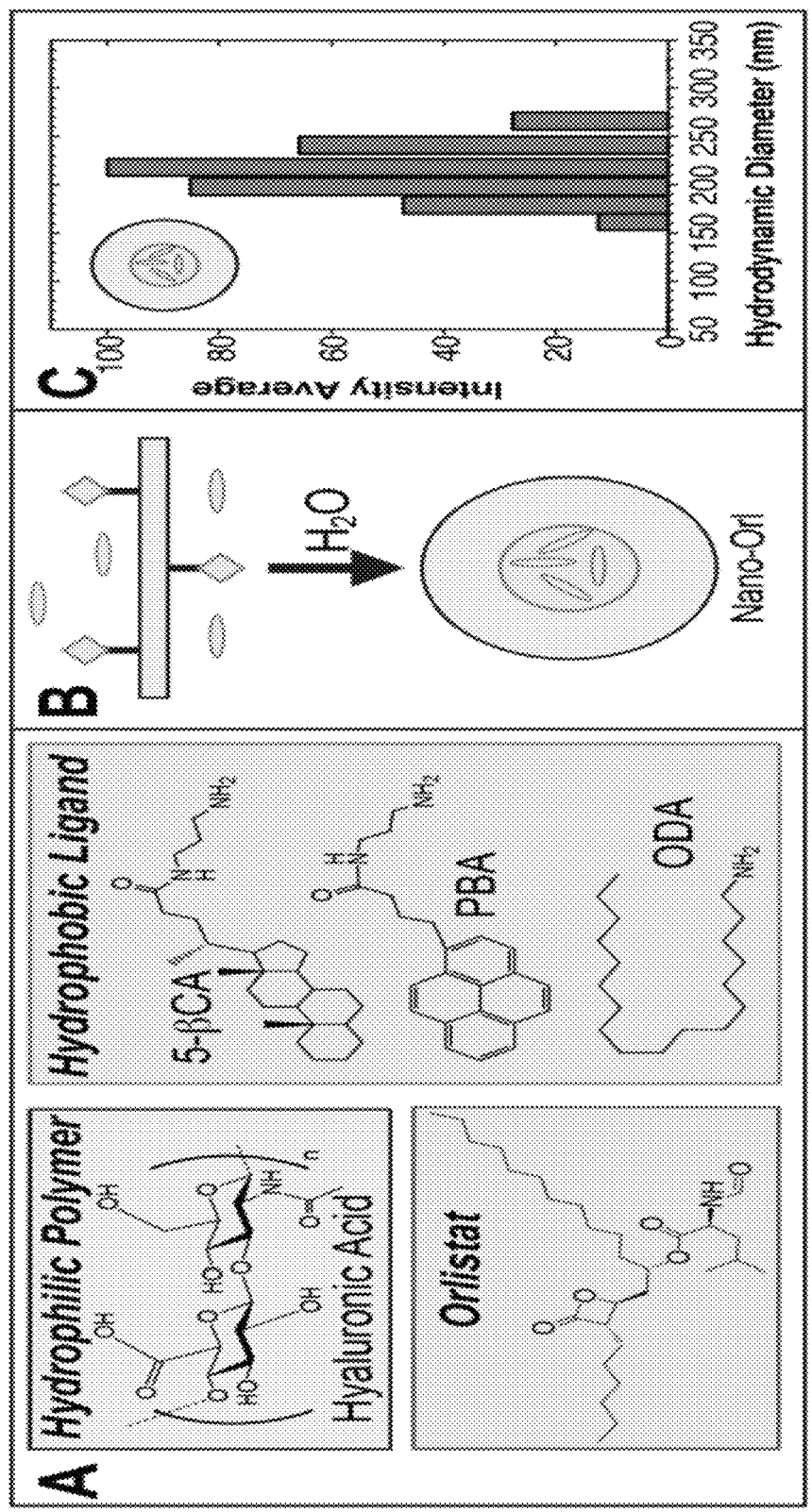
FIG. 2 shows (A) Chemical structures of hyaluronic acid (HLA), hydrophobic ligands, and Orlistat. (B) Amphiphilic HLA (from conjugation of hydrophobic ligand and HLA) self-assembles in aqueous buffers to entrap hydrophobic Orlistat. (C) Representative DLS characterization of Nano-Orl indicate that Nano-Orl is approximately 200 nm in HD.
Figure 3:
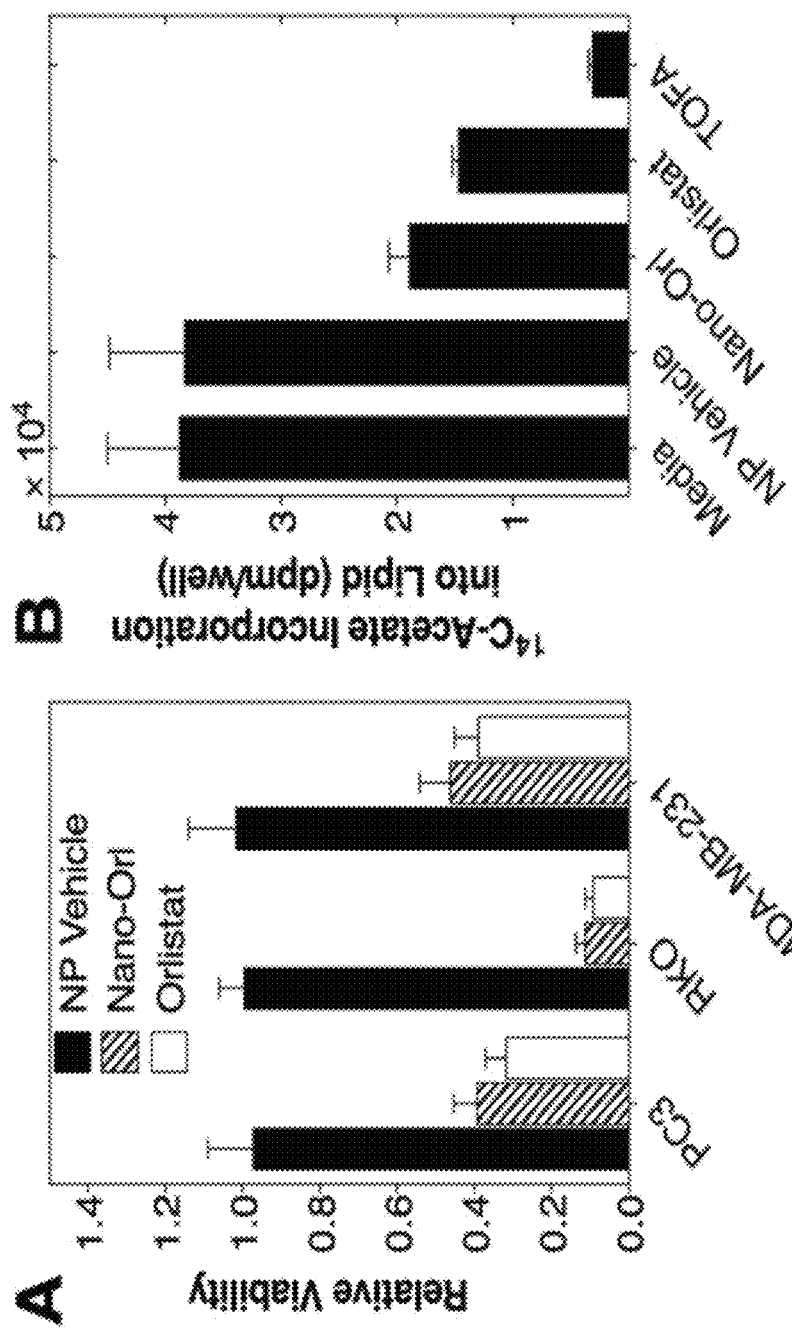
FIG. 3 shows A) Cytotoxicity of Nano-Orl, NP Vehicle, and free Orlistat to multiple cells lines. (B) Using PC3 cells as an example cell line, Nano-Orl inhibited FASN mediated incorporation of acetate in lipids similar to free Orlistat and a positive control, TOFA.

Expected Results and Alternative Strategies:

Due to the hydrophobicity of Orlistat, it is believed that a very high percentage of the Orlistat will be entrapped due to self-assembly of amphiphilic HLA. FIGS. 2-4 support this assertion because of the comparable cytotoxicity, level of fatty acid synthesis, and the NP formulation to render Orlistat effective even after prolonged exposure in aqueous conditions. However, if loading capacity is substantially lower than expected, alternative hydrophobic ligands will be evaluated to identify more optimal loading of Orlistat. The largest technical difficulty will be the quantification of Orlistat loaded within the nanoparticle. To supplement the approach presented above, SEC may be used to first isolate Nano-Orl. An appropriate solvent will then be used to disassemble the NP formulation and it will then be subjected HPLC-MS to quantify Orlistat. It is known that Orlistat inhibits tumor growth in vivo compared to a sham control. It is anticipated that NP entrapment of Orlistat will increase in vivo efficacy because of overall preferential accumulation of nanoparticles in the tumor microenvironment. Unexpected factors such as off-site toxicity or serum protein interaction may limit Orlistat dosing or delivery to the tumor site and efficacy of the proposed therapeutic Nano-Orl could be diminished. In this case, second generation Nano-Orl with optimized colloidal properties will be developed and they will be evaluated for tumor efficacy and minimized off-target toxicity.

Develop Second Generation Nano-Orl with Optimized Stability and Controlled Release In an embodiment, the present invention relates to first generation development of Nano-Orl (as shown in the data above), which is as effective in vitro as free Orlistat. In one variation, it is also shown that Nano-Orl acts by inhibiting FASN, and improves stability of Orlistat in aqueous media. Thus, there are two key advantages to using HLA-based NPs. First, HLA is a ligand for CD44 and second HLA can be degraded by HYAL. These properties could render Nano-Orl specifically targetable to CD44 positive tumors with controlled release due to HYAL. This specific aim investigates two synthetic modifications to Nano-Orl, develops the techniques to study controlled release of Orlistat from Nano-Orl, and studies the relationship between controlled release and cytotoxicity due to Orlistat.

Synthesis of Second Generation Nano-Orl.

Variable Molecular Weight Amphiphilic HLA.

Nano-Orl will be synthesized with HLA of two different number average molecular weights, 10 kDa and 100 kDa; with both available from Lifecore Biomedical (Chaska, Minn.). Consistent with the data, PBA will serve as the lead hydrophobic ligand and will be conjugated to HLA via NHS/EDC coupling. In one embodiment of the present invention, it has been confirmed that higher MW HLA is reactive to HYAL after hydrophobic modification (data not shown). Due to the higher molecular weight, it is believed that optimal conjugation of PBA will need to be modified to facilitate optimal loading of Orlistat. Based on data not shown, increasing the molecular weight of HLA creates larger NPs, and as a result, should entrap more Orlistat per nanoparticle. Thus, in an embodiment of the invention, the present invention relates to Nano-Orl compositions that comprise different size NPs, such as any number average molecular weights between about 10 kDa and 200 kDa, or alternatively, between about 10 kDa and 100 kDa.

Poly(Ethylene Glycol) (PEG) Stabilized Nano-Orl.

It is known that PEG decreases nonspecific protein interaction. This can result in increased blood circulation times and, in this case, may also prevent nonspecific degradation of HLA and unwanted release of Orlistat. Accordingly, in one embodiment of the invention, amine functionalized PEG (Rapp Polymere, Tübingen, Germany) will be grafted to the carboxyl groups of HLA based on protocols established by the present inventors. The inventors' studies indicate that PEG (mw=550-2000 Da) added to biodegradable paramagnetic contrast agents greatly increased plasma half-life of the agents. Accordingly, in one embodiment, grafting with PEG of 500 Da and 2,000 Da will be performed. Moreover, in an embodiment, the present invention will evaluate grafting with PEG of 3000 Da and 10,000 Da.

Quantify the Extent and Rate of Orlistat Release from Nano-Orl

Orlistat release from Nano-Orl due to nonspecific HLA degradation and to specific HYAL interaction will be determined based on a method modified from Dolenc, et al. (52). Dialysis tubing (Spectrum, 12,000-14,000 MWCO) will be presoaked in dissolution media (1-3% SDS in PBS). Next, Nano-Orl will be suspended in pH 7.2 PBS and then diluted in a 1:1 ratio of Nano-Orl solution to 2× dissolution media containing 400 U/ml HYAL-1 resulting in NPs suspended in 1× (1-3% SDS, 200 U/ml HYAL-1) degradation media. The dialysis tubing containing Nano-Orl in degradation media will then be immediately placed in a bath of dissolution media (no HYAL-1) under constant stirring. Control samples using solely dissolution media in the dialysis bag will be used as a control to determine the release of Orlistat due to SDS; extracted pure Orlistat will be used as a reference. At appropriate time points, aliquots of sample in the dialysis bag will be subjected to HPLC analysis to determine the concentration of Orlistat. The concentration of Orlistat will be measured prior to dissolution studies and at 5, 10, 15, 30, and 60 min and 2, 4, 8, 24, and 48 h after exposure to dissolution media in the presence and absence of HYAL-1. Release will be measured as percent Orlistat remaining in the tubing relative to freshly suspended Nano-Orl. Aim 2.3. Relationship between colloidal stability and cytotoxicity.

Cytotoxicity.

The cytotoxicity of Nano-Orl will be evaluated using PC3, MDA-MB-231, RKO, and normal cell lines. The following groups will be tested for cytotoxicity: Nano-Orl with different molecular weight HLAs, PEGylated Nano-Orl, the various corresponding NP vehicles, stock Orlistat, as well as media only controls. Because NP entrapment of Orlistat could change the efficacy and the kinetics of cytotoxicity, Nano-Orl will be screened for a wide range of Orlistat concentrations and time points. The cytotoxicity will be determined using a WST-8 assay (Dojindo, Inc.).

Acetate Incorporation.

Orlistat acts by inhibiting FASN thioesterase function and ultimately FA production. $^{14}$C-acetate incorporation into fatty acids will be measured to confirm that the toxicity of Nano-Orl is due to FASN inhibition. Cells will be incubated with Nano-Orl, NP vehicle, Orlistat, or media for a time optimized based on controlled release kinetics of Orlistat from second generation Nano-Orl. Next, 1 µCi of $^{14}$C-acetate will be added to the cells and be incubated for an additional 2 h. After washing cells with PBS/EDTA, the fatty acids will be extracted with chloroform/methanol (1:1) and quantified by scintillation counting using standard protocols.

Mitochondrial Capacity.

Figure 6:
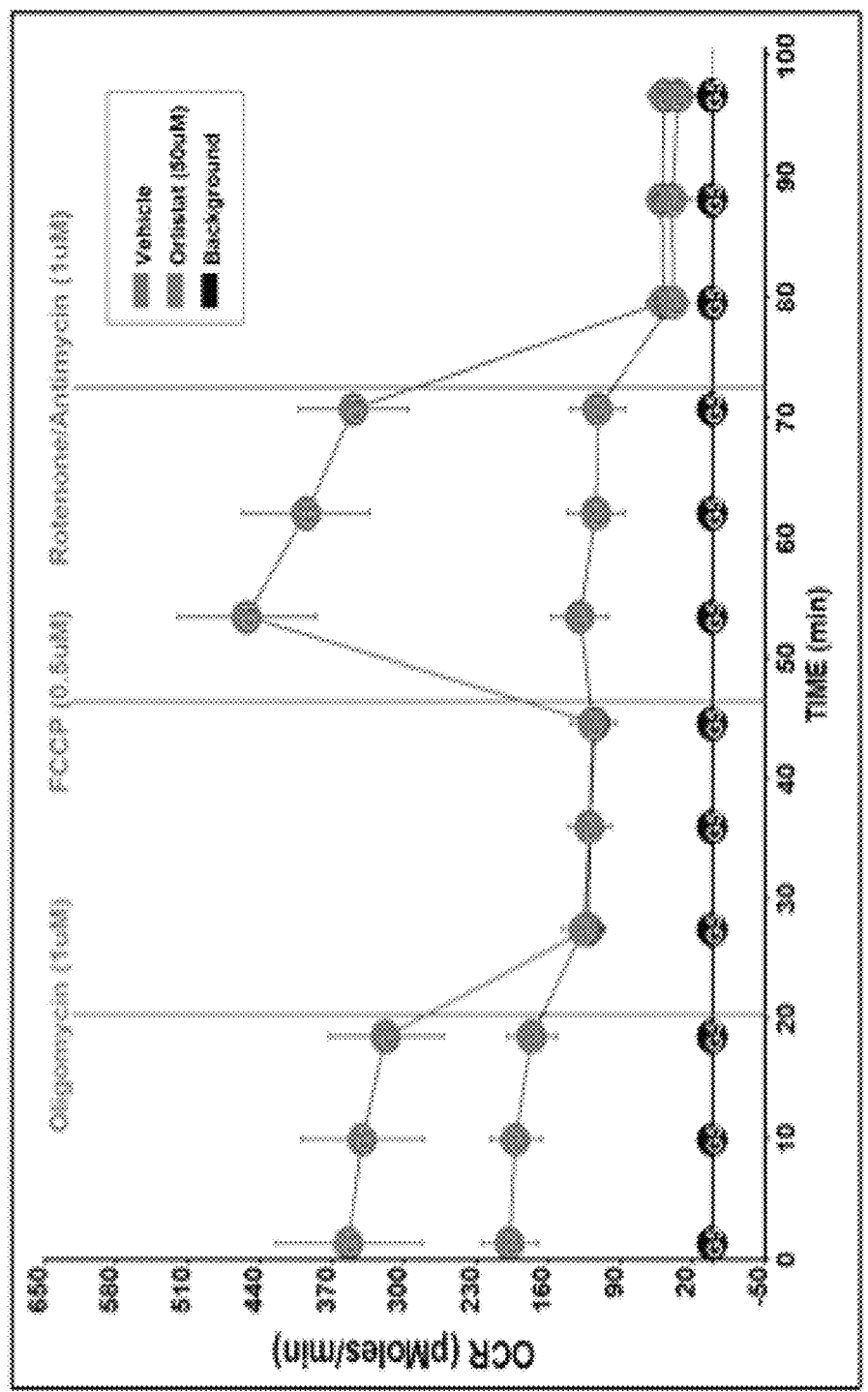
FIG. 6 shows Orlistat decreases mitochondrial capacity in tumor cells. PC3 cells were seeded into 24-well XF analysis microplates. The cells were the treated with vehicle (•) or Orlistat (50 µM, ※) for 12 hours before analysis, according to Seahorse protocols. Oxygen consumption rate (OCR), a measure of mitochondrial capacity, was determined using a Seahorse Mito Stress test on a Seahorse XF24 extracellular flux analyzer.

FASN can regulate mitochondrial function through multiple mechanisms. It can regulate membrane composition and it can also affect metabolic flux through different pathways. The data as shown in FIG. 6 demonstrates that Orlistat negatively impacts mitochondrial capacity. Cells seeded in XF24 analysis microplates will be treated with NP vehicle, Nano-Orl, orlistat, or formulation buffer. The mitochondrial capacity, as determined by oxygen consumption rate (OCR), will be measured by the Seahorse Mito Stress kit (Seahorse Bioscience, Boston, Mass.). Oligomycin is an ATP synthase inhibitor, FCCP is an ETC accelerator, and rotenone/anitmycin inhibit complex I. Seahorse analysis will indicate initial OCR rates for each treatment and oligoycin treatment will indicate overall ATP production, FCCP treatment will measure maximal respiratory capacity and rotenone/antimycin will indicate spare respiratory capacity.

Expected Results and Alternative Strategies:

By increasing the HLA molecular weight, it is believed that an increase in the amount of Orlistat loaded per NP will occur. PEG is widely regarded for preventing nonspecific protein interaction. It is thus possible that PEG will interfere with HYAL-facilitated degradation of Nano-Orl. If this is the case, less bulky hydrophilic polymers will be explored to minimize nonspecific interactions. Thus in an embodiment the present invention relates to a method to quantify Orlistat release from Nano-Orl. SDS will be used in one variation in the dissolution media to provide sink conditions for Orlistat. HYAL-1 activity will be evaluated in dilute solutions of SDS (1-3%) prior to release studies. If HYAL-1 loses significant activity in the presence of dilute solutions of SDS, alternative dissolution and alternative sink conditions will be tested, such as the inclusion of proteins. Thus, in an embodiment, the present invention relates to using dilute solutions of SDS (1-3% by weight), with the optional inclusion of proteins.

Figure 7:
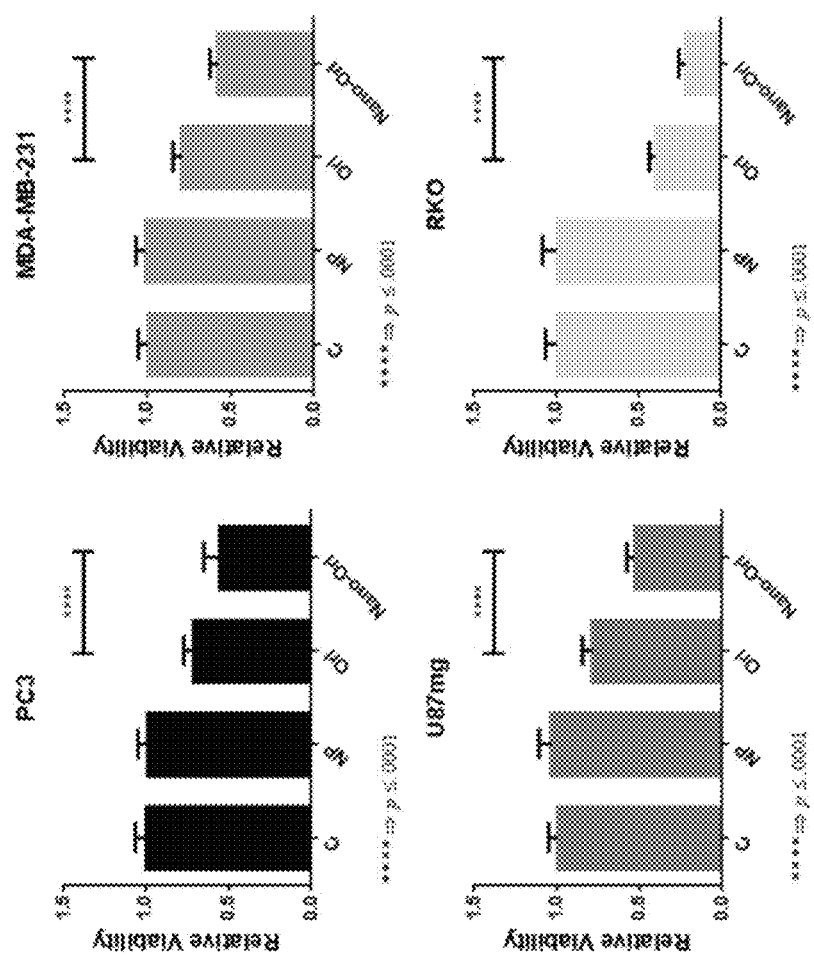
FIG. 7 shows Nano-Orl and free Orlistat incubated with one of four cancer cell lines for 48 hours. The total Orlistat concentration was the same in both the Nano-Orl and Orlistat groups (25 micro-molar). A CCK-8 metabolic assay was then used to measure cytotoxic effect at 48 hours, and groups were normalized to control cells which received no treatment.

FIG. 7 shows Nano-Orl and free Orlistat incubated with one of four cancer cell lines for 48 hours. The total Orlistat concentration was the same in both the Nano-Orl and Orlistat groups (25 micro-molar). A CCK-8 metabolic assay was then used to measure cytotoxic effect at 48 hours, and groups were normalized to control cells which received no treatment. The results show that the Nano-Orl formulation has a greater cytotoxic effect than free Orlistat ($p<0.0001$ in all cell lines). This increased toxicity does not appear to be the result of the nanoparticle material, as empty nanoparticles exhibited no cytotoxicity. Rather, the higher toxicity exhibited by Nano-Orl compared to free Orlistat is likely due to an increase in the aqueous stability and solubility of the Nano-Orl formulation, which allows for more effective and prolonged delivery of Orlistat to the cells.

Thus, in an embodiment, the present invention relates to compounds, compositions and methods comprising nanoparticles (NP) that are based on hyaluronic acid (HLA) that have been modified with hydrophobic moieties that can entrap FASN inhibitor compounds. In one variation, the FASN inhibitor compounds will include Orlistat. In one variation, the hydrophobic moieties comprise 5-βCA, Pba, or ODA, or combinations thereof. In a variation, the present invention relates to a composition comprising NPs based upon HLA, Orlistat, one or more of the hydrophobic moieties comprising 5-βCA, Pba, or ODA, and one or more of members selected from the group consisting of PEG and a dilute solution containing SDS. In a variation, the HLA containing NPs will comprise a number average molecular weight between about 10 kDa and 100 kDa.

In one variation, other inhibitors that may be used include Cerulenin, Quercetin Dihydrate, Kaempferol, C75 (4-Methylene-2-octyl-5-oxotetrahydrofuran-3-carboxylic acid), Luteolin, BML-275 (Dorsomorphin), Pyrazinamide, Platensimycin, and Triclosan.

In one variation, the compounds and compositions as discussed above will be used to treat a subject that is in need of cancer treatment.

In an embodiment, the composition may be a pharmaceutical composition that is ideally suited to the type of delivery that provides the most efficacious treatment.

In a variation, the present invention relates to pharmaceutical compositions and methods using those pharmaceutical compositions. The pharmaceutical composition may contain pharmaceutically acceptable salts, solvates, and prodrugs thereof, and may contain diluents, excipients, carriers, or other substances necessary to increase the bioavailability or extend the lifetime of the compounds and/or compositions of the present invention.

Subjects that may be treated by the compounds and compositions of the present invention include, but are not limited to, horses, cows, sheep, pigs, mice, dogs, cats, primates such as chimpanzees, gorillas, rhesus monkeys, and, humans. In an embodiment, a subject is a human in need of cancer treatment.

In an embodiment, the compounds, compositions and methods of the present invention can be used in combination with radiation therapy for treating diseases of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination thereof.

Alternatively, in an embodiment, the compositions, compounds and methods of the present invention can be used for colon, head and neck, hepatocellular, non-small cell lung, prostate and breast cancers.

The pharmaceutical compositions containing a compound of the invention may be in a form suitable for injection either by itself or alternatively, using liposomes, micelles, and/or nanospheres.

In an embodiment, the compositions of the present invention may be used as injectables. The composition intended for injection may be prepared according to any known method, and such compositions may contain one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycethanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents.

Oily suspensions may be formulated by suspending the active ingredient in a vegetable oil, for example *arachis* oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or *arachis* oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate.

The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Thus, in another embodiment, the present invention provides a pharmaceutical formulation solution comprising the conjugate(s) or compositions as described herein or salts thereof.

A solution of the invention may be provided in a sealed container, especially one made of glass, either in a unit dosage form or in a multiple dosage form.

Any pharmaceutically acceptable salt of a compound of the conjugate(s) as described herein may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the conjugate(s) as described herein is a hydrochloric acid salt including a mono, di, or trihydrochloride.

Any solvent which is pharmaceutically acceptable and which is able to dissolve the conjugate(s) as described herein or a pharmaceutically acceptable salt thereof may be used. The solution of the invention may also contain one or more additional components such as a co-solubilizing agent(s) (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may suitable for a solution formulation are described below.

Suitable solvents and co-solubilizing agents may include, but are not limited to, water; sterile water for injection (SWFI); physiological saline; alcohols, e.g. ethanol, benzyl alcohol and the like; glycols and polyalcohols, e.g. propyleneglycol, glycerin and the like; esters of polyalcohols, e.g.

diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise the conjugate(s) as described herein or a pharmaceutically acceptable salt thereof, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the conjugate(s) as described herein or a pharmaceutically acceptable salt thereof may be less than 100 mg/mL, or less than 50 mg/mL, or less than 10 mg/mL, or less than 10 mg/mL and greater than 0.01 mg/mL, or between 0.5 mg/mL and 5 mg/mL, or between 1 mg/mL and 3 mg/mL. In an embodiment, the concentration that is used is the ideal concentration to be used for identification purposes and/or to be sufficiently cytotoxic to the cancer cells yet limit the toxicity on other cells.

Suitable packaging for the pharmaceutical solution formulations may be all approved containers intended for parenteral use or intravenous use, such as plastic and glass containers, ready-to-use syringes and the like. In an embodiment, the container is a sealed glass container, e.g. a vial or an ampoule. A hermetically sealed glass vial is particularly preferred.

According to an embodiment of the present invention, there is provided, in a sealed glass container, a sterile, injectable solution comprising the conjugate(s) and/or compositions as described herein or a pharmaceutically acceptable salt thereof in a physiologically acceptable solvent, and which has a pH of from 2.5 to 3.5. For solution formulations, various compounds and/or compositions of the present invention may be more soluble or stable for longer periods in solutions at a pH lower than 6. Further, acid salts of the compounds and/or compositions of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving the conjugate(s) as described herein or a pharmaceutically acceptable salt thereof in a pharmaceutically acceptable solvent. Where a pharmaceutically acceptable acid salt of the conjugate(s) as described herein is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

One or more additional components such as co-solubilizing agents, tonicity adjustment agents, stabilizing agents and preservatives, for instance of the kind previously specified, may be added to the solution prior to passing the solution through the sterilizing filter.

In a further variation, the present invention contemplates combination therapies in which the compounds and/or compositions of the present invention can be used in conjunction with other compositions of the present invention. It is also contemplated and therefore within the scope of the invention that other anti-neoplastic agents/compounds can be used in conjunction with the compounds and/or compositions of the present invention. The anti-neoplastic agents/compounds that can be used with the compounds and/or compositions of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab).

Other anti-neoplastic agents/compounds that can be used in conjunction with the compounds and/or compositions of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds and/or compositions of the present invention include Campath, IL-8, B-FGF, Tek antagonists, anti-TWEAK agents (e.g., specifically binding antibodies or antigen binding regions, or soluble TWEAK receptor antagonists, ADAM distintegrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other anti-angiogenic/anti-tumor agents that can be used in conjunction with the compounds and/or compositions of the present invention include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA); ilomastat, (Arriva, USA,); emaxanib, (Pfizer, USA,); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland); the ARGENT technology of Ariad, USA; YIGSR-Stealth, (Johnson & Johnson, USA); fibrinogen-E fragment, (Bio-Acta, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142, (Fujisawa, Japan); platelet factor 4, (RepliGen, USA); vascular endothelial growth factor antagonist, (Borean, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford Bio-Medica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Children's Hospital, USA); ATN 161, (Attenuon, USA); ANGIOSTATIN, (Boston Children's Hospital, USA); 2-methoxyestradiol, (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Children's Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI 4610, (Sima, USA); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

It is contemplated and therefore within the scope of the invention that the compounds and/or compositions of the present invention can be modified to target specific receptors or cancer cells or can be modified so that they can survive various in vivo environments. In a variation, the conjugates, compositions, and methods of the present invention can be used against solid tumors, cell lines, and cell line tissue that demonstrate upregulated nucleotide excision repair and other upregulated resistance mechanisms.

It is contemplated and therefore within the scope of the present invention that any feature that is described above can be combined with any other feature that is described above. When conjugates and/or compositions are discussed, it should be understood that those conjugates and/or compositions are contemplated as being parts of methods of identifying tumors, methods of treatment and/or methods of making. Moreover, it should be understood that the present invention contemplates minor modifications that can be made to the compounds, conjugates, compositions and methods of the present invention. In any event, the present invention is defined by the below claims.

The following references are incorporated by reference in their entireties:

1. Menendez J A, Lupu R. Fatty acid synthase and the lipogenic phenotype in cancer pathogenesis. Nat Rev Cancer. 2007 October; 7(10):763-77.
2. Kuhajda F P. Fatty-acid synthase and human cancer: new perspectives on its role in tumor biology. Nutrition. 2000 March; 16(3):202-8.
3. Hanahan D, Weinberg R A. Hallmarks of cancer: the next generation. Cell. 2011 March; 144(5):646-74.
4. Kuhajda F P, Jenner K, Wood F D, Hennigar R A, Jacobs L B, Dick J D, Pasternack G R. Fatty acid synthesis: a potential selective target for antineoplastic therapy. Proc Natl Acad Sci USA. 1994 July; 91(14):6379-83.
5. Kuhajda F P. Fatty Acid Synthase and Cancer: New Application of an Old Pathway. Cancer Res. 2006 Jun. 15; 66(12):5977-80.
6. Zhou W, Han W F, Landree L E, Thupari J N, Pinn M L, Bililign T, Kim E K, Vadlamudi A, Medghalchi S M, Meskini El R, Ronnett G V, Townsend C A, Kuhajda F P. Fatty acid synthase inhibition activates AMP-activated protein kinase in SKOV3 human ovarian cancer cells. Cancer Res. 2007 April; 67(7):2964-71.
7. Zhou W, Simpson P J, McFadden J M, Townsend C A, Medghalchi S M, Vadlamudi A, Pinn M L, Ronnett G V, Kuhajda F P. Fatty acid synthase inhibition triggers apoptosis during S phase in human cancer cells. Cancer Res. 2003 November; 63(21):7330-7.
8. Selvendiran K, Ahmed S, Dayton A, Ravi Y. HO-3867, a synthetic compound, inhibits the migration and invasion of ovarian carcinoma cells through downregulation of fatty acid synthase and focal adhesion Kinase. Molecular Cancer Research. 2010 September; 8(9):1188-97.
9. Turrado C, Puig T, García-Cárceles J, Artola M, Benhamú B, Ortega-Gutiérrez S, Relat J, Oliveras G, Blancafort A, Haro D, Marrero P F, Colomer R, López-Rodríguez M L. New Synthetic Inhibitors of Fatty Acid Synthase with Anticancer Activity. J Med Chem. 2012 May; 55(11): 5013-23.
10. Puig T, Aguilar H, Cufi S, Oliveras G, Turrado C, Ortega-Gutiérrez S, Benhamú B, López-Rodríguez M L, Urruticoechea A, Colomer R. A novel inhibitor of fatty acid synthase shows activity against HER2+ breast cancer xenografts and is active in anti-HER2 drug-resistant cell lines. Breast Cancer Res. 2011 December; 13(6):R131.
11. Puig T, Turrado C, Benhamú B, Aguilar H, Relat J, Ortega-Gutiérrez S, Casals G, Marrero P F, Urruticoechea A, Haro D, López-Rodríguez M L, Colomer R. Novel Inhibitors of Fatty Acid Synthase with Anticancer Activity. Clin Cancer Res. 2009 December; 15(24):7608-15.
12. Kridel S J, Axelrod F, Rozenkrantz N, Smith J W. Orlistat is a novel inhibitor of fatty acid synthase with antitumor activity. Cancer Res. 2004 March; 64(6):2070-5.
13. Pemble C W, Johnson L C, Kridel S J, Lowther W T. Crystal structure of the thioesterase domain of human fatty acid synthase inhibited by Orlistat. Nat Struct Mol Biol. 2007 July; 14(8):704-9.
14. Little J L, Wheeler F B, Koumenis C, Kridel S J. Disruption of crosstalk between the fatty acid synthesis and proteasome pathways enhances unfolded protein response signaling and cell death. Mol Cancer Ther. 2008 December; 7(12):3816-24.
15. Alivisatos P. The use of nanocrystals in biological detection. Nat Biotechnol. Nature Publishing Group; 2004 January; 22(1):47-52.
16. Ferrari M. Cancer nanotechnology: opportunities and challenges. Nat Rev Cancer. 2005 March; 5(3):161-71.
17. Gao X, Cui Y, Levenson R, Chung L, Nie S. In vivo cancer targeting and imaging with semiconductor quantum dots. Nat Biotech. 2004; 22(8):969-76.
18. La Zerda de A, Zavaleta C, Keren S, Vaithilingam S, Bodapati S, Liu Z, Levi J, Smith B, Ma T, Oralkan O, Cheng Z, Chen X, Dai H, Khuri-Yakub B, Gambhir S. Carbon nanotubes as photoacoustic molecular imaging agents in living mice. Nat Nanotechnol. 2008 September; 3(9):557-62.
19. Wang X, Li J, Wang Y, Koenig L, Gjyrezi A, Giannakakou P, Shin E H, Tighiouart M, Chen Z G, Nie S, Shin D M. A Folate Receptor-Targeting Nanoparticle Minimizes Drug Resistance in a Human Cancer Model. ACS Nano. 2011 August; 5(8):6184-94.
20. Hood J D, Bednarski M, Frausto R, Guccione S, Reisfeld R A, Xiang R, Cheresh D A. Tumor regression by targeted gene delivery to the neovasculature. Science. 2002 June; 296(5577):2404-7.
21. Eliasof S, Lazarus D, Peters C G, Case R I, Cole R O, Hwang J, Schluep T, Chao J, Lin J, Yen Y, Han H, Wiley D T, Zuckerman J E, Davis M E. Correlating preclinical animal studies and human clinical trials of a multifunctional, polymeric nanoparticle. Proc Natl Acad Sci USA. 2013 September; 110(37):15127-32.
22. Torchilin V P. Micellar nanocarriers: pharmaceutical perspectives. Pharm Res. 2007 January; 24(1):1-16.
23. Kopecek J. Polymer-drug conjugates: Origins, progress to date and future directions. Advanced Drug Delivery Reviews. 2013 January; 65(1):49-59.
24. Sharifi S, Behzadi S, Laurent S, Laird Forrest M, Stroeve P, Mahmoudi M. Toxicity of nanomaterials. Chemical Society reviews. 2012; 41(6):2323-43.
25. Wang A Z, Wang A Z, Langer R, Langer R, Farokhzad O C, Farokhzad O C. Nanoparticle Delivery of Cancer Drugs. Annu Rev Med. 2012 January; 63(1):185-98.
26. Zhang L, Gu F X, Chan J M, Wang A Z, Langer R S, Farokhzad O C. Nanoparticles in medicine: therapeutic applications and developments. Clin Pharmacol Ther. 2008 May; 83(5):761-9.
27. Matsumura Y, Maeda H. A new concept for macromolecular therapeutics in cancer chemotherapy: mechanism of tumoritropic accumulation of proteins and the antitumor agent smancs. Cancer Res. 1986 December; 46(12 Pt 1):6387-92.
28. Livney Y D, Assaraf Y G. Rationally designed nanovehicles to overcome cancer chemoresistance. Adv Drug Deliv Rev. 2013 November; 65(13-14):1716-30.
29. Druker B J, Talpaz M, Resta D J, Peng B, Buchdunger E, Ford J M, Lydon N B, Kantarjian H, Capdeville R, Ohno-Jones S, Sawyers C L. Efficacy and safety of a specific inhibitor of the BCR-ABL tyrosine kinase in chronic myeloid leukemia. New England Journal of Medicine. 2001 April; 344(14):1031-7.
30. Romond E H, Perez E A, Bryant J, Suman V J, Geyer C E, Davidson N E, Tan-Chiu E, Martino S, Paik S, Kaufman P A, Swain S M, Pisansky T M, Fehrenbacher L, Kutteh L A, Vogel V G, Visscher D W, Yothers G, Jenkins R B, Brown A M, Dakhil S R, Mamounas E P, Lingle W L, Klein P M, Ingle J N, Wolmark N. Trastuzumab plus adjuvant chemotherapy for operable HER2-positive breast cancer. N Engl J Med. 2005 October; 353(16): 1673-84.
31. Kogan G, Soltés L, Stern R, Gemeiner P. Hyaluronic acid: a natural biopolymer with a broad range of biomedical and industrial applications. Biotechnol Lett. Kluwer Academic Publishers; 2007 January; 29(1):17-25.
32. Toole B P. Hyaluronan: from extracellular glue to pericellular cue. Nat Rev Cancer. 2004 July; 4(7):528-39.
33. Gaffney J, Matou-Nasri S, Grau-Olivares M, Slevin M. Therapeutic applications of hyaluronan. Mol. BioSyst. The Royal Society of Chemistry; 2010; 6(3):437-43.
34. Aruffo A, Stamenkovic I, Melnick M, Underhill C B, Seed B. CD44 is the principal cell surface receptor for hyaluronate. Cell. 1990 June; 61(7):1303-13.
35. Wang S J, Bourguignon L Y W. Role of hyaluronan-mediated CD44 signaling in head and neck squamous cell carcinoma progression and chemoresistance. Am J Pathol. 2011 March; 178(3):956-63.
36. Zöller M. CD44: can a cancer-initiating cell profit from an abundantly expressed molecule? Nat Rev Cancer. 2011 April; 11(4):254-67.
37. Gires O. Lessons from common markers of tumor-initiating cells in solid cancers. Cell Mol Life Sci. 2011 December; 68(24):4009-22.
38. Stern R, Jedrzejas M J. Hyaluronidases: Their Genomics, Structures, and Mechanisms of Action. Chem Rev. 2006 March; 106(3):818-39.
39. Stern R. Hyaluronidases in cancer biology. Seminars in Cancer Biology. 2008 August; 18(4):275-80.
40. Dhir R, Gau J, Krill D, Bastacky S, Bahnson R, Cooper D, Becich M. CD44 Expression in Benign and Neoplastic Human Prostates. Mol. Diagn. 1997 September; 2(3):197-204.
41. Patrawala L, Calhoun T, Schneider-Broussard R, Li H, Bhatia B, Tang S, Reilly J G, Chandra D, Zhou J, Claypool K, Coghlan L, Tang D G. Highly purified CD44+ prostate cancer cells from xenograft human tumors are enriched in tumorigenic and metastatic progenitor cells. Oncogene. 2006 January; 25(12):1696-708.
42. Lokeshwar V B, Lokeshwar B L, Pham H T, Block N L. Association of elevated levels of hyaluronidase, a matrix-degrading enzyme, with prostate cancer progression. Cancer Res. 1996 February; 56(3):651-7.
43. Lokeshwar V B, Cerwinka W H, Isoyama T, Lokeshwar B L. HYAL1 hyaluronidase in prostate cancer: a tumor promoter and suppressor. Cancer Res. 2005 September; 65(17):7782-9.
44. Kovar J L, Johnson M A, Volcheck W M, Chen J, Simpson M A. Hyaluronidase Expression Induces Prostate Tumor Metastasis in an Orthotopic Mouse Model. The American Journal of Pathology. 2006 October; 169 (4):1415-26.
45. Jin Y-J, Termsarasab U, Ko S-H, Shim J-S, Chong S, Chung S-J, Shim C-K, Cho H-J, Kim D-D. Hyaluronic Acid Derivative-Based Self-Assembled Nanoparticles for the Treatment of Melanoma. Pharm Res. Springer U S; 2012; 29(12):3443-54.
46. Choi K Y, Chung H, Min K H, Yoon H Y, Kim K, Park J H, Kwon I C, Jeong S Y. Self-assembled hyaluronic acid nanoparticles for active tumor targeting. Biomaterials. 2010 January; 31(1):106-14.

We claim:

1. A pharmaceutical composition for treating cancer comprising nanoparticles that are based on hyaluronic acid that have been modified with one or more hydrophobic moieties, and an active ingredient comprising a fatty acid synthase (FASN) inhibitor compound entrapped in the one or more hydrophobic moieties wherein the hyaluronic acid has a number average molecular weight less than 100 KDa.

2. The pharmaceutical composition of claim 1 wherein the FASN inhibitor compound is Orlistat.

3. The pharmaceutical composition of claim 2, wherein the one or more hydrophobic moieties comprise 5-β-cholanamide (5-βCA), 4-(pyrene-1-yl)butanamide (Pba), or octadecylamine (ODA), or combinations thereof.

4. The pharmaceutical composition of claim 3, further comprising one or more of members selected from the group consisting of polyethylene glycol (PEG) and a dilute solution containing sodium dodecyl sulfate (SDS).

5. The pharmaceutical composition of claim 4, wherein PEG is present at a size of between about 500 Da and 2,000 Da.

6. The pharmaceutical composition of claim 4, wherein the dilute solution containing SDS is present in an amount that is about between 1% and 3% by weight SDS.

7. The pharmaceutical composition of claim 5, further comprising one or more inhibitors that comprise Cerulenin, Quercetin Dihydrate, Kaempferol, C75 (4-Methylene-2'octyl-5-oxotetrahydrofuran-3-carboxylic acid), Luteolin, BML-275 (Dorsomorphin) Pyrazinamide, Platensimycin, or Triclosan.

8. The pharmaceutical composition of claim 5, wherein the composition is administered intravenously to a subject that has cancer.

9. The pharmaceutical composition of claim 3, further comprising one or more of pharmaceutically acceptable salts, diluents, excipients, carriers, stabilizers, co-solubilizing agents, tonicity adjustment agents, preservatives, pH adjusting agents, wetting agents, suspending agents, emulsifying agents, thickening agents, chelating agents, antioxidants, reducing agents, antimicrobial preservatives, buffers, bulking agents, protectants, tonicity adjustors, or special additives.

10. The pharmaceutical composition of claim 4, further comprising one or more of pharmaceutically acceptable salts, excipients, carriers, stabilizers, co-solubilizing agents, tonicity adjustment agents, preservatives, pH adjusting agents, wetting agents, suspending agents, emulsifying agents, thickening agents, chelating agents, antioxidants, reducing agents, antimicrobial preservatives, buffers, bulking agents, protectants, tonicity adjustors, or special additives.

11. The pharmaceutical composition of claim 5, further comprising one or more of pharmaceutically acceptable salts, diluents excipients, carriers, stabilizers, co-solubilizing agents, tonicity adjustment agents, preservatives, pH adjusting agents, wetting agents, suspending agents, emulsifying agents, thickening agents, chelating agents, antioxidants, reducing agents, antimicrobial preservatives, buffers, bulking agents, protectants, tonicity adjustors, or special additives.

12. A method of treating cancer comprising administering to a subject in need thereof a pharmaceutically effective amount of the composition of claim 1.

13. The method of claim 12, wherein the cancer is selected from the group consisting of colon, head and neck, hepatocellular, non-small cell lung, prostate and breast cancers.

14. The method of claim 12, wherein the one or more FASN inhibitor compounds is Orlistat.

15. The method of claim 14, wherein the one or more hydrophobic moieties comprise 5-βCA, Pba, or ODA, or combinations thereof.

16. The method of claim 15, wherein the composition further comprises one or more members selected from the group consisting of PEG and a dilute solution containing SDS.

17. The method of claim 16, wherein when PEG is present, PEG is present at a size of between about 500 Da and 2,000 Da, and when the dilute solution containing SDS is present, the dilute solution containing SDS is present in an amount that is about between 1% and 3% by weight SDS.

18. The method of claim 15, wherein the composition is administered intravenously to the subject that has cancer.

19. The method of claim 15, wherein the composition further comprises one or more of pharmaceutically acceptable salts, diluents, excipients, carriers, stabilizers, co-solubilizing agents, tonicity adjustment agents, preservatives, pH adjusting agents, wetting agents, suspending agents, emulsifying agents, thickening agents, chelating agents, antioxidants, reducing agents, antimicrobial preservatives, butlers, bulking agents, protectants, tonicity adjustors, or special additives.

20. The pharmaceutical composition of claim 1, wherein the hyaluronic acid has an average molecular weight about 10 kDa.

21. The pharmaceutical composition of claim 1, wherein the one or more hydrophobic moieties comprise 4-(pyrene-1-yl)butanamide (Pba).

22. The pharmaceutical composition of claim 1, wherein the active ingredient consists of Orlistat and one or more inhibitors selected from the group consisting of Cerulenin, Quercetin Dihydrate, Kaempferol, C75 (4-Methylene-2,octyl-5-oxotetrahydrofuran-3-carboxylic acid), Luteolin, BML-275 (Dorsomorphin) Pyrazinamide, Platensimycin, and Triclosan.

* * * * *